(12) United States Patent
 Chaffringeon

(10) Patent No.: US 10,779,996 B2
(45) Date of Patent: Sep. 22, 2020

(54) VAGINAL INSERTION ASSEMBLY

(71) Applicant: V-VEIL-SHOP LTD., Nicosia (CY)

(72) Inventor: Bernard Chaffringeon, Lausanne (CH)

(73) Assignee: V-VEIL-UP-PHARMA LIMITED, Nicosia (CY)

( * ) Notice: Subject to any disclaimer, the term of this patent is extended or adjusted under 35 U.S.C. 154(b) by 903 days.

(21) Appl. No.: 14/898,985

(22) PCT Filed: Jun. 5, 2014

(86) PCT No.: PCT/IB2014/061970
§ 371 (c)(1),
(2) Date: Dec. 16, 2015

(87) PCT Pub. No.: WO2014/203107
PCT Pub. Date: Dec. 24, 2014

(65) Prior Publication Data
US 2016/0120708 A1    May 5, 2016

(30) Foreign Application Priority Data

Jun. 17, 2013 (RO) ................................ a201300457

(51) Int. Cl.
*A61F 13/15* (2006.01)
*A61F 13/20* (2006.01)
(Continued)

(52) U.S. Cl.
CPC ........ *A61F 13/2062* (2013.01); *A61F 13/204* (2013.01); *A61F 13/2025* (2013.01);
(Continued)

(58) Field of Classification Search
CPC ................ A61F 13/2025; A61F 13/204; A61F 13/2062; A61F 13/2074; A61F 13/266;
(Continued)

(56) References Cited

U.S. PATENT DOCUMENTS 1,884,089 A    10/1932    Millner
3,335,726 A *  8/1967    Maranto ................. A61F 13/26
                                                         604/12

(Continued)

FOREIGN PATENT DOCUMENTS

| WO | 2006123132 A1 | 11/2006 |
| WO | 2009112527 A1 | 9/2009 |
| WO | 2012114200 A2 | 8/2012 |

OTHER PUBLICATIONS

European Patent Office, International Search Report, Written Opinion of the International Searching Authority, and International Preliminary Report on Patentability for PCT/IB2014/061970, International Filing Date Jun. 5, 2014, Priority Date Jun. 17, 2013.

*Primary Examiner* — Michele M Kidwell
(74) *Attorney, Agent, or Firm* — Law Office of Andrei D Popovici, PC

(57) ABSTRACT

The invention relates to a vaginal insertion assembly and methods of manufacturing it, which comprises a flexible retention web made by an atraumatic material intended to be introduced into the vaginal cavity with the aid of an applicator, said web comprising removal means and a shorter web flap F1 obtained by strangling the web in a site P, and being arranged into the applicator such that the web becomes more rigid and makes it less penetrable.

12 Claims, 11 Drawing Sheets

(51) Int. Cl.
*A61F 13/26* (2006.01)
*A61F 13/34* (2006.01)

(52) U.S. Cl.
CPC ...... *A61F 13/2074* (2013.01); *A61F 13/2082* (2013.01); *A61F 13/2094* (2013.01); *A61F 13/2097* (2013.01); *A61F 13/266* (2013.01); *A61F 13/34* (2013.01)

(58) Field of Classification Search
CPC .. A61F 13/34; A61F 13/2082; A61F 13/2094; A61F 13/2097
See application file for complete search history.

(56) References Cited

U.S. PATENT DOCUMENTS

| | | | | |
|---|---|---|---|---|
| 3,559,646 A * | 2/1971 | Mullan | .................... | A61F 13/26 604/15 |
| 4,211,225 A * | 7/1980 | Sibalis | ................ | A61F 13/2051 604/385.18 |
| 4,212,301 A | 7/1980 | Johnson | | |
| 4,318,405 A * | 3/1982 | Sneider | ................ | A61K 9/0036 604/15 |
| 4,341,214 A * | 7/1982 | Fries | .................... | A61F 13/2048 604/365 |
| 4,610,659 A * | 9/1986 | Friese | .................... | A61F 15/003 604/11 |
| 4,675,217 A * | 6/1987 | Forsman | .............. | A61F 13/2051 428/121 |
| 6,183,436 B1 * | 2/2001 | Korteweg | ........... | A61F 13/2051 28/118 |
| 6,635,800 B2 * | 10/2003 | Jackson | .............. | A61F 13/2068 604/378 |
| 7,192,421 B2 * | 3/2007 | Hasse | .................... | A61F 13/206 604/385.18 |
| 7,713,253 B2 * | 5/2010 | Osborn, III | ........... | A61F 13/202 604/385.17 |
| 9,814,629 B2 * | 11/2017 | Chaffringeon | ...... | A61F 13/2062 |
| 2003/0149392 A1 * | 8/2003 | Arnould | .................. | A61F 13/26 604/15 |
| 2004/0225272 A1 * | 11/2004 | Karapasha | .......... | A61F 13/2068 604/385.17 |
| 2005/0197615 A1 * | 9/2005 | Gann | ..................... | A61F 13/26 604/11 |
| 2006/0258971 A1 * | 11/2006 | Chase | .................... | A61F 13/26 604/12 |
| 2013/0030392 A1 * | 1/2013 | Chaffringeon | .......... | A61F 13/26 604/286 |

* cited by examiner

VAGINAL INSERTION ASSEMBLY

The present invention relates to an assembly used for the insertion of a flexible retention web into the vaginal cavity with the purpose of absorbing discharges of bodily fluids and/or administering a therapeutic or non-therapeutic agent.

Conventional tampons are known to be used inside the vaginal cavity with the purpose of absorbing discharges of bodily fluids, especially menstrual flows. These tampons are made of absorbent materials able to retain moderate or even substantial flow. This kind of tampons can be relatively uncomfortable when they are inserted or extracted from the vaginal cavity, due to the friction between the walls of the vagina and the absorbent material.

There is a general concern in finding materials and designs for the tampons in order to provide more comfort to the user when they are inserted or extracted from the vaginal cavity.

To this purpose, patent U.S. Pat. No. 4,212,301 discloses a digital tampon of unitary construction made of absorbent material, a portion thereof being compressed to a rod-like shape to provide a rigid central support for the remaining relatively uncompressed portion which originates at the top of the rigid central support and drops downwardly to surround and extend past the lower terminus of the support. This construction allows structural support during insertion and external conformability for comfort.

Patent document U.S. Pat. No. 1,884,089 discloses a sanitary article in the form of a disc which is folded around the finger and thus introduced into the vaginal cavity. The disc is made of a highly compressed absorbent material and has means of removal attached to its center.

However, such sanitary articles are not designed for reduced flow of bodily discharges, i.e. under 6 g. By using such articles, the user may experience high discomfort especially during the removal of the tampon due to the contact between the dry wall of the vagina and the dry surface of the tampon.

In order to avoid this drawback, patent application EP2276441 discloses a flexible retention web for low and very low flow of bodily fluids, intended to be introduced into the vaginal cavity and provided with means of removal. Such a web is particularly designed to afford exceptional comfort to a user who produces small amounts of bodily discharge, for example as a result of regular use of a contraceptive, or whose menstrual flow is limited, particularly at the end of the menstrual cycle. Such a web can be introduced into the vaginal cavity with the aid of a finger or a pushing tool.

International patent application published under no WO2012/114200 provides a device for inserting a web according to EP2276441 into the vaginal cavity, comprising an applicator member having an at least partially hollow end that is intended to be inserted inside the vaginal cavity and which defines inside an internal volume and a flexible retention web equipped with a means for removal, the web comprising a central zone, housed in the internal volume and a peripheral zone that covers said applicator's end at the exterior. A pouch if formed in the internal volume by the web, in which a therapeutic or non-therapeutic agent may be inserted (such as a capsule, suppository or cream) that is delivered inside the vaginal cavity.

By using such a device, when the web is delivered inside the vaginal cavity, it is possible that the pouch does not unfold, keeping therein the therapeutic or non-therapeutic agent. Thus, said agent will only partially reach the zone to be treated. Part of the agent will remain into the pouch and will be removed together with the web, thus reducing the effectiveness of the treatment, so that greater quantities of agent will be needed in order to ensure the desired effect.

Also, when placing low viscosity agents within said pouch, such as low viscosity creams or liquids, they can easily pass through the web material into the applicator, thus the quantity delivered inside the vaginal cavity will be reduced to an amount that cannot be measured.

To eliminate these drawbacks, the present invention provides a vaginal insertion assembly comprising:
  an at least partially hollow body applicator (A), having a grip portion (G) and a head portion (H) intended to be inserted into the vaginal cavity (V), said head portion (H) being hollow and ending with an open section (O)
  a flexible retention web (W) for insertion into the vaginal cavity of a user with the aid of said applicator (A), which web is made of an atraumatic material and is provided with means for removal (R),
  characterized in that
  the flexible retention web (W) is strangled at a site (P) along its transverse axis, thus defining a shorter web flap (F1) and a longer web flap (F2),
  the shorter web flap (F1) is at least partially housed within the head portion (H) of the applicator (A), with the site (P) oriented downwards, towards the grip portion (G) and the free end (E1) oriented upwards,
  and the longer web flap (F2) protrudes through the open section (O) and covers at least partially the body of the applicator, such that the central zone of the web remains outside.

As used herein, the expression "the web is strangled at a site P" is to be understood that the length of the transversal axis of the web at site P is significantly shorter than the length of any other transversal axis situated in the vicinity thereof. The strangling may be effected, for example, by welding, ultrasound welding, sewing, weaving, knotting (lasso or choker type), adhesion or any method that allows a strangling effect.

As a consequence of the strangling of the web at site P, the shorter web flap F1 will have a folded shape, i.e. in the form of multiple folds such as a fan or spiral folds, etc. This arrangement will confer rigidity to said shorter flap F1 and makes it less penetrable.

For an easy detachment of the web from the applicator, the inventor has found that more than half of the web's surface, containing also the central zone thereof, must be outside and covering the applicator's body.

When the assembly according to the invention is inserted into the vaginal cavity, the vaginal opening exerts an annular pressure on the web covering the applicator's body. This pressure is substantial enough to pinch the web and when the applicator is thrusted by the user, it will result in the unrolling of the web. A longer portion of the web protruding outside the applicator will result in a longer duration of the contact between the vaginal opening and the web, thus ensuring that the shorter flap F1 is extracted from the head portion H of the applicator by the end of the insertion of the assembly into the vaginal cavity.

It should be noted that, as opposed to a device disclosed in WO2012/114200 in which the central zone of the web is housed inside the applicator's body, the assembly according to the invention provides an efficient extraction of the web from the applicator, during insertion into the vaginal cavity, with significantly less web material.

If a therapeutic or non-therapeutic agent was previously placed on the top of the free end E1, said agent is more efficiently pushed inside the vaginal cavity, due to the rigidity of the shorter flap F1, ensuring a direct contact of the agent with the vaginal wall. When using such an assembly, no pouch can be formed by the web inside the vaginal cavity, thus providing total contact between the agent and the vaginal wall.

Preferably, the ratio between the length (L1) of the shorter web flap, defined as the length between the site (P) and the extremity (E1) of the shorter flap (F1), opposite to the site of attachment, and the length (L2) of the longer web flap, defined as the length between the site (P) and the extremity (E2) of the longer flap (F2) opposite to the site of attachment, is at most ¼, more preferably between about 1/12 and ¼.

Typically, the length of the web is smaller than 20 cm. Particularly, the length of the web is about 13 cm and the shorter web flap F1 is shorter than 2.6 cm, preferably between 0.5 and 2.5 cm.

The assembly according to the invention may be used as a sanitary article that retains and/or slows down low flow bodily discharges and/or as a tool for delivering therapeutic or non-therapeutic agents inside the vaginal cavity.

Within the meaning of the present invention, the expression "low flow bodily discharges" refers, for example, to a flow of less than 6 g, which can be as a result of a regular use of a contraceptive or in a user whose menstrual flow is limited, such as at the end of the cycle. More specifically, an assembly according to the invention may be suitable for low or medium-intensity metrorrhagia, for example upon changing contraceptive pills or after placing an intrauterine contraceptive device, in women with physiological leucorrhea or after sexual intercourse, to collect the sexual discharges.

The web according to the invention may be more or less absorbent, depending on the desired use. Moreover, said web may be made of a non-expandable or minimally expandable material, meaning that the capacity of expansion or of dilation of the web is not like that of a traditional tampon in which the core is designed to dilate in order to be able to absorb a maximum quantity of fluid. Also, the thickness of the web according to the invention is usually much smaller compared to a normal tampon.

Advantageously, such a web is made of a material chosen from the group comprising in particular a non-woven textile, polyvinyl acetate, cotton, an organic material, or a plant material. Particularly, this material may be biodegradable.

The web can preferably have a substantially rectangular, square, oval or circular shape, for example.

Moreover, the web is designed such that it can convey at least one therapeutic and/or non-therapeutic agent that has, for example, healing, lubricating, anticoagulant or antioxidant properties, into the vaginal cavity. For this purpose, the web may be, for example, impregnated with such a therapeutic and/or non-therapeutic agent or may support the at least one agent on it, for example in the form of hard or soft capsule, suppository, cream or dry vaginal suppository.

According to one feature of the invention, the web incorporates at least one fluid barrier formed with the aid of a hydrophobic material, for example petroleum jelly, Vaseline or beeswax.

The dimensions of the web may be chosen so that, after application, it remains completely contained within the vaginal cavity.

Alternatively, the dimensions of the web may be chosen so that, after application, it partially obstructs the vaginal opening into the vulva. This has the effect that the leaking of fluids from the vaginal cavity is almost completely prevented.

Yet in another alternative embodiment, the dimensions of the web may be chosen so that, after application, part of the web protrudes outside of the vaginal cavity, reaching the vulva. Preferably, the part of the web that protrudes outside has the dimensions suitable for use as a pantiliner. This arrangement has the effect that the web acts both as an internal tampon, retaining the discharges from the vaginal cavity and also as a pantiliner, absorbing the outside humidity from vulva's area, i.e. from urinary incontinence or perspiration. Preferably, the part of the web that protrudes outside the vaginal cavity is fringed. Also preferably, the part of the web that protrudes outside may be used as removal means for the extraction of the web from the vaginal cavity.

In a preferred embodiment, the removal means is attached to the web at the site P and the applicator is hollow.

The removal means may be, for example, at least one string, strip, ribbon, wire, etc. with a length adapted for the extraction of the web from the vaginal cavity and may be made of any material which does not tear when a force necessary to extract the web from the vaginal cavity is applied. Advantageously, the applicator is made in the form of a tubular body.

Also advantageously, the head of the applicator is made in the form of a substantially conical segment, so as to have a reduced passage section relative to the diameter of the applicator's body, and the head has radial elasticity.

The present invention also relates to a method of manufacturing a vaginal insertion assembly comprising the steps of:
  cutting a flexible retention web into the desired form and dimensions, for example into rectangular shape
  strangling the web along its transverse axis such as to form a smaller web flap of less than ¼ of the material's length, for example by welding, ultrasound welding, sewing, weaving, knotting (lasso or choker type), adhesion or any method that allows a strangling effect.
  attaching to the web at least one string forming removal means in a desired point such as to allow the easy extraction of the web from the vaginal cavity
  inserting the free ends of each string into the body of the applicator
  pulling the free ends of at least one string to insert at least partially the shorter flap F1, which is folded over the rest of the web material on the point of attachment P, into the head portion P of the applicator A, such that the site (P) is oriented downwards, towards the grip portion (G) of the applicator A and the free end (E1) is oriented upwards It is to be understood that these steps may be also executed in a different order, if desired.

Alternatively, the shorter flap F1 may be inserted into the applicator, after bending it over the rest of the web, by pushing with the aid of an insertion member. In this embodiment, the removal means may pass through the applicator or outside it. In this latter case, the applicator may be only partially hollow, such that it allows the housing of the shorter web flap F1 into the head portion H.

The vaginal insertion assembly according to the invention may be used to provide a flexible retention web, made of an atraumatic material, with the dimensions adapted so as to be able to retain and/or slow down bodily discharges of small quantity, inside the vaginal cavity of a user.

Alternatively, the vaginal insertion assembly may be used together with a therapeutic and/or non-therapeutic agent.

For example, if said agent is in the form, for example, of a soft or hard capsule or a suppository, the shorter web flap F1 is completely housed into the head portion H of the applicator, with the free end E1 oriented towards the open section O of the head portion H, so that it allows the agent to be positioned on the free end E1, at least partially inside the head portion H of the applicator, for delivery into the vaginal cavity.

Preferably, the capsule may have the form of a mushroom, with the stalk being placed inside the head portion H, on the free end E1, and the cap covering the open section O. More preferably, said capsule starts melting immediately when in contact with the vaginal mucosa. This has a lubricating effect, allowing an easy and painless insertion and removal of the applicator inside and out of the vaginal cavity.

Alternatively, if said agent is in the form of a cream or gel, or even a liquid, the shorter web flap F1 is at least partially housed into the head portion H of the applicator, with the point of attachment P oriented towards the grip portion G of the applicator and the agent can be placed on the free end E1 by means of, for example, an injecting tool, a spatula, a dropper bottle or any other way. According to another embodiment, the free end E1 protrudes outside the head portion H of the applicator and may be dipped into said agent.

Embodiments of the invention will now be described by way of example with reference to the accompanying drawings wherein:

FIG. 1 shows a diagrammatic perspective view of a web according to a preferred embodiment of the invention FIGS. 2 and 3 are longitudinal cross-sectional views of a vaginal insertion assembly according to different embodiments FIG. 4 shows a longitudinal cross-sectional view of an example illustrating a way of applying a therapeutic or non-therapeutic agent in the form of a cream, gel or liquid on the free end E1 of the shorter flap F1 of the flexible retention web W FIGS. 5 and 6 show longitudinal cross-sectional views of a preferred embodiment illustrating 3 successive steps for releasing a mushroom type capsule inside the vaginal cavity FIGS. 7 and 8 show longitudinal cross-sectional views of different embodiments illustrating arrangements of the flexible retention web after removal of the applicator FIG. 9 shows a diagrammatic perspective view of a web according to another preferred embodiment of the invention, in which the web protrudes outside the vaginal cavity after insertion therein FIG. 10 shows a front view of the vulva after the insertion of a web according to an embodiment of the invention in which part of the web which is fringed protrudes outside of the vaginal cavity.

FIG. 11 shows diagrammatic longitudinal cross-sectional views illustrating the successive steps of manufacturing an assembly according to an embodiment of the invention.

In FIG. 1 a rectangular flexible retention web according to one embodiment of the invention is strangled at a site P defining a shorter web flap F1 having a length L1 between the site P and the free end E1, located opposite to site P and a longer web flap F2 having a length L2 between site P and the free end E2, located opposite to site P and E1. Removal means are attached to the web. Preferably, the removal means are attached at the site P.

FIG. 2 shows a vaginal insertion assembly according to an embodiment of the invention in which the shorter flap F1 is completely housed inside the head portion H of the applicator A. The shorter flap F1 is bended over the rest of the web at site P and is housed inside the applicator A with the site P towards the grip portion G of the applicator, such that a therapeutic or non-therapeutic agent may optionally be placed on the free end E1 of the shorter flap F1.

FIG. 3 is the illustration of an alternative embodiment to the one in FIG. 2, in which the shorter web flap F1 is partially protruding outside the head portion P through the opening O of the applicator, allowing, for instance, the dipping of the free end E1 into a non-solid therapeutic or non-therapeutic agent. Advantageously, the longer web flap F2 is folded onto itself at least once.

FIG. 4 illustrates a way of applying a non-solid therapeutic or non-therapeutic agent, for example in the form of a cream, gel or liquid, to the vaginal insertion assembly, for delivery into the vaginal cavity. Said agent is placed on the top of the free end E1 of the shorter flap F1 and because of the shape formed inside the applicator's head portion H by the shorter flap F1, the leakage of the agent is prevented.

FIG. 5a shows the right position of a mushroom type capsule into the vaginal insertion assembly according to the present invention, before insertion into the vaginal cavity. The shorter flap F1 is completely housed inside the head portion H of the applicator allowing also the stalk of the mushroom type capsule to be at least partially placed inside the head portion H, on top of the free end E1, or slightly above it. The cap of the capsule is covering the open section O of the applicator's head portion O, allowing a good lubrication.

FIG. 5b shows and intermediary position of the mushroom type capsule, when it is released inside the vaginal cavity. When the applicator is removed, after insertion of the assembly into the vaginal cavity, the shorter flap F1 pushes the capsule, which, due to the higher weight of the cap, falls on the top of the free end E1 and, as seen in FIG. 6, contacts the vaginal walls and melts, allowing the delivery of the therapeutic or non-therapeutic agent to the desired location.

FIG. 7 illustrates a preferred embodiment in which the dimensions of the flexible retention web are adapted so that, after application, the web at least partially obstructs the vaginal opening T into the vulva.

Alternatively, FIG. 8 illustrates yet another preferred embodiment, in which the dimensions of the flexible retention web are adapted so that, after application, part of the web protrudes outside of the vaginal cavity, reaching the vulva.

Figure 1:
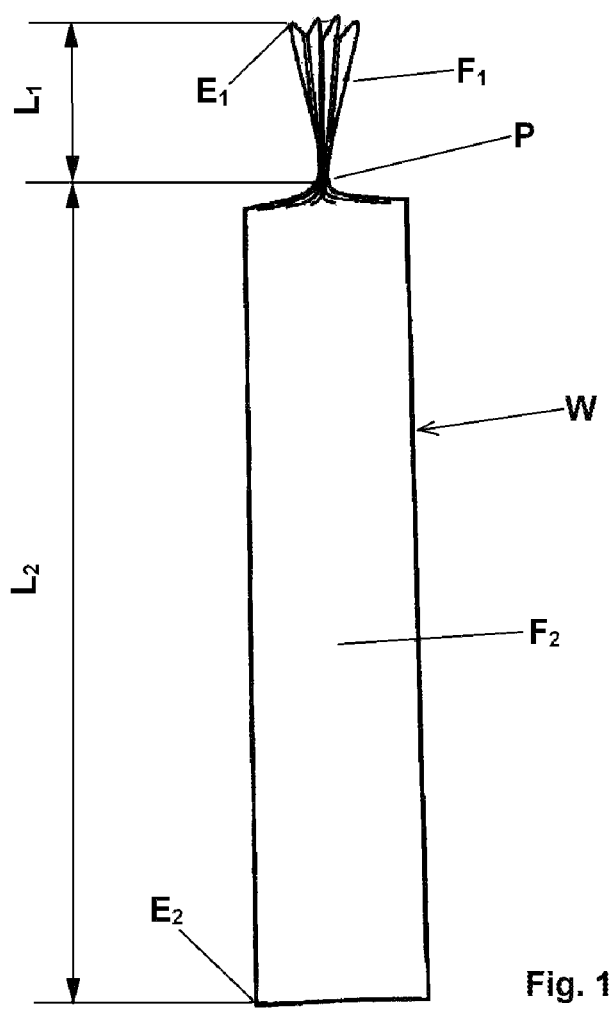
Figure 2:
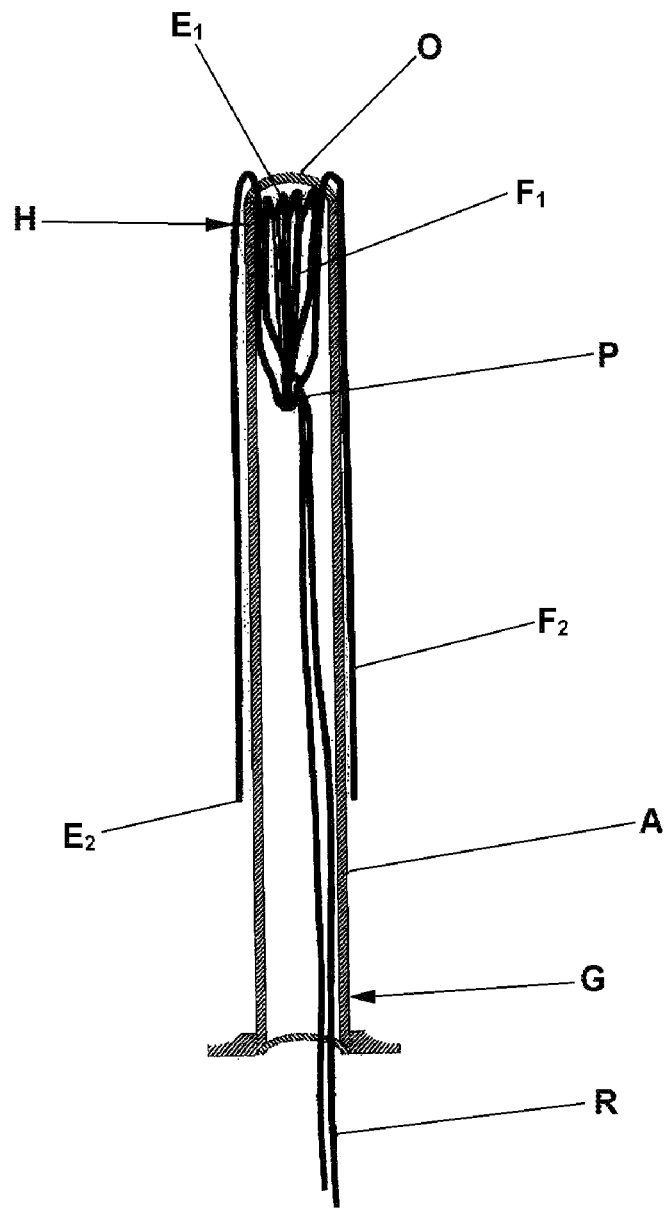
Figure 3:
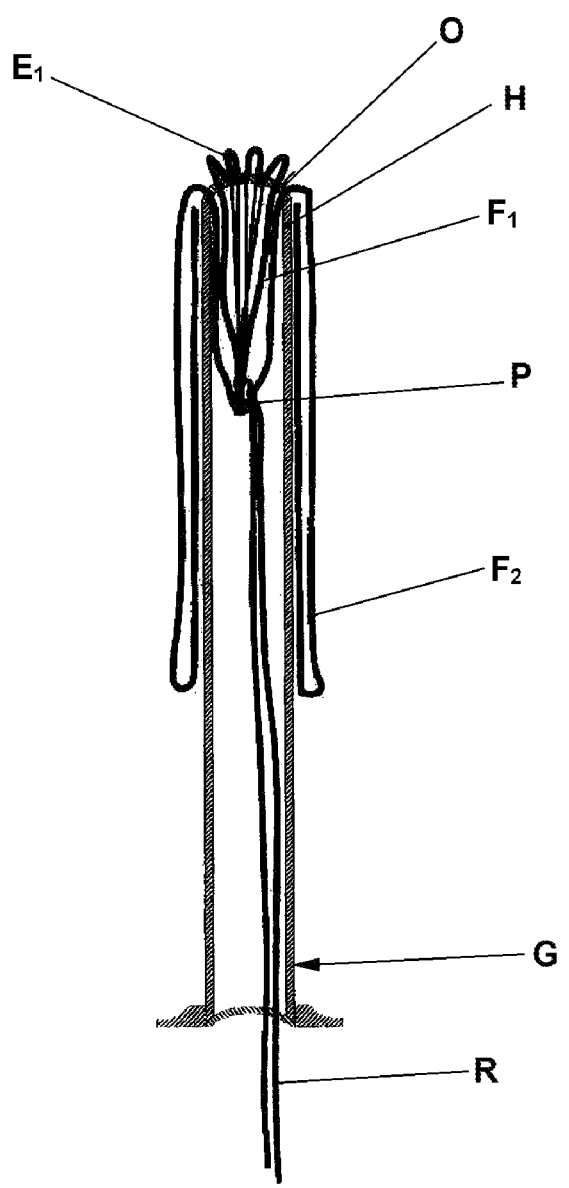
Figure 4:
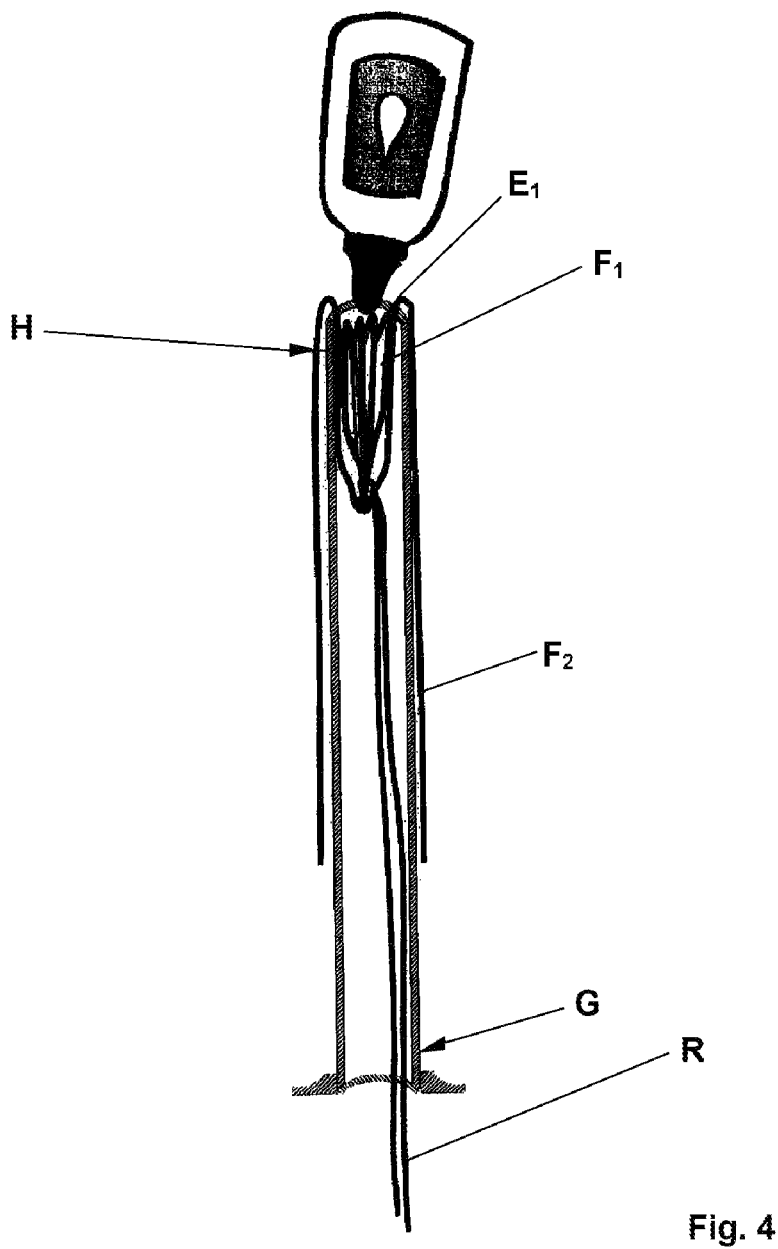
Figure 5:
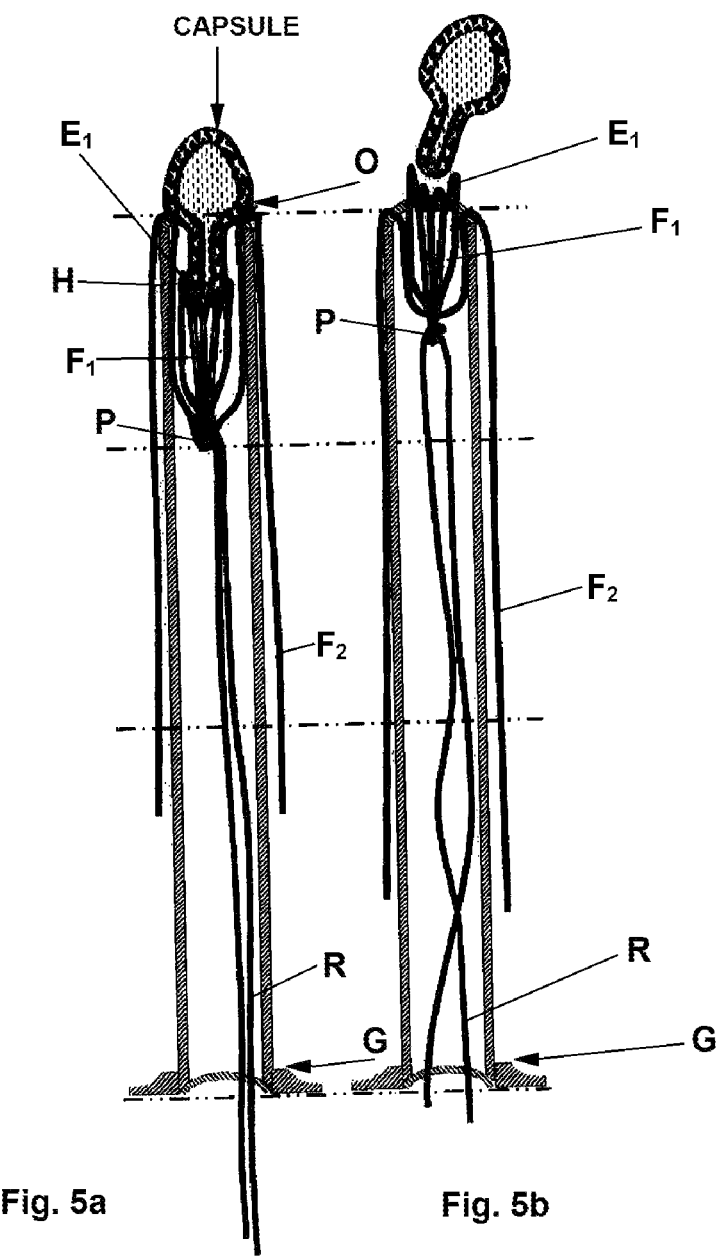
Figure 6:
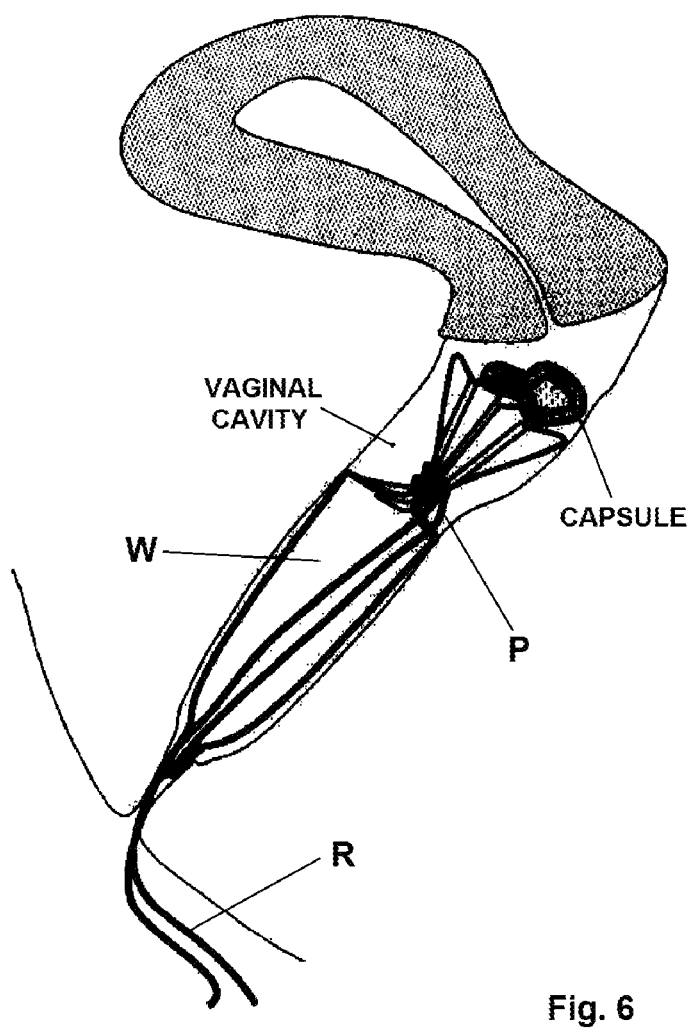
Figure 7:
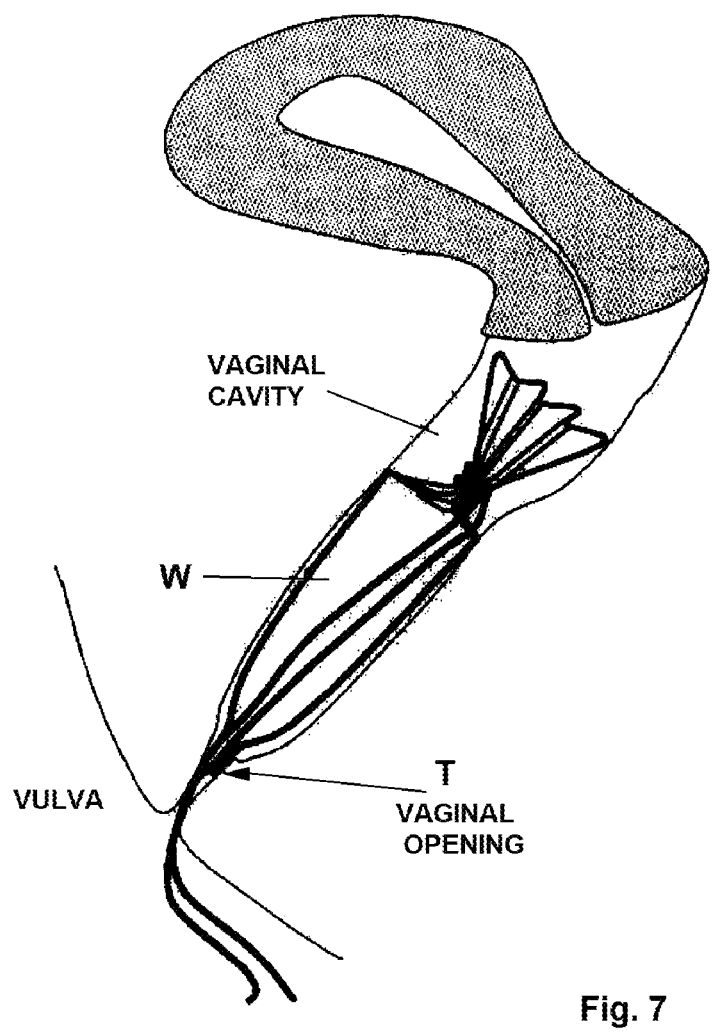
Figure 8:
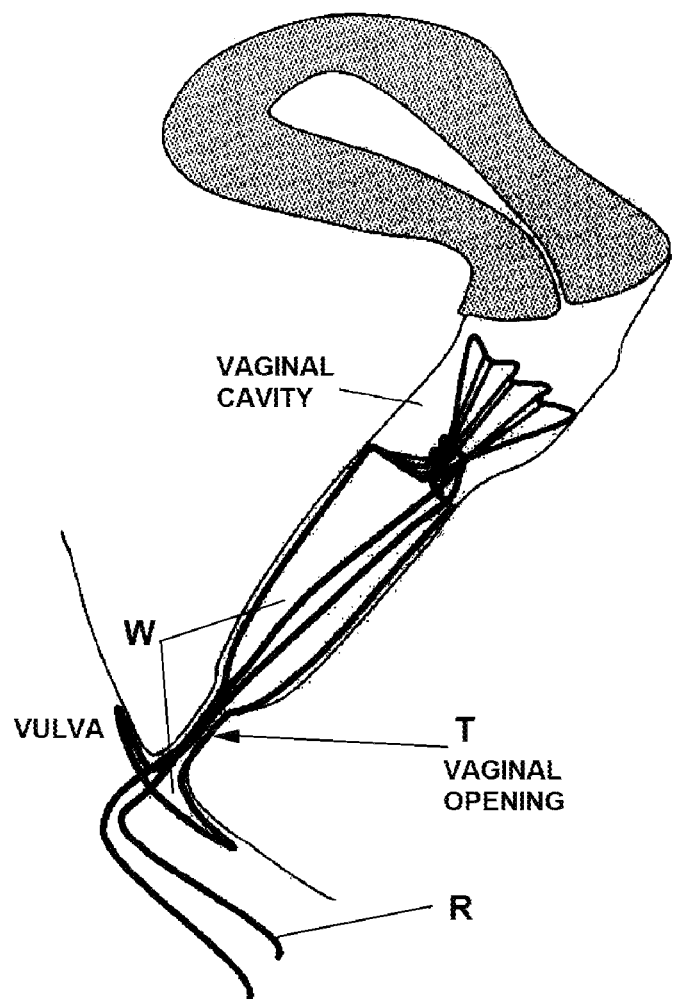
Figure 9:
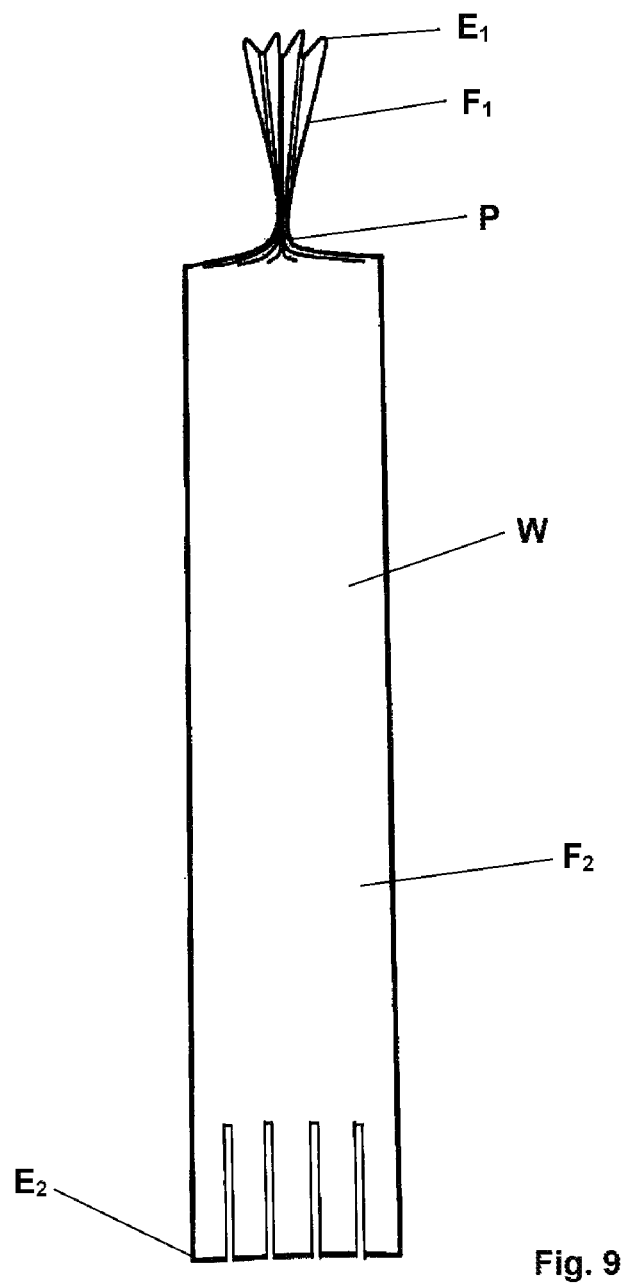
FIG. 9 shows an alternative preferred embodiment to FIG. 1 in which the web is fringed at the end that protrudes outside the vaginal cavity.
Figure 10:
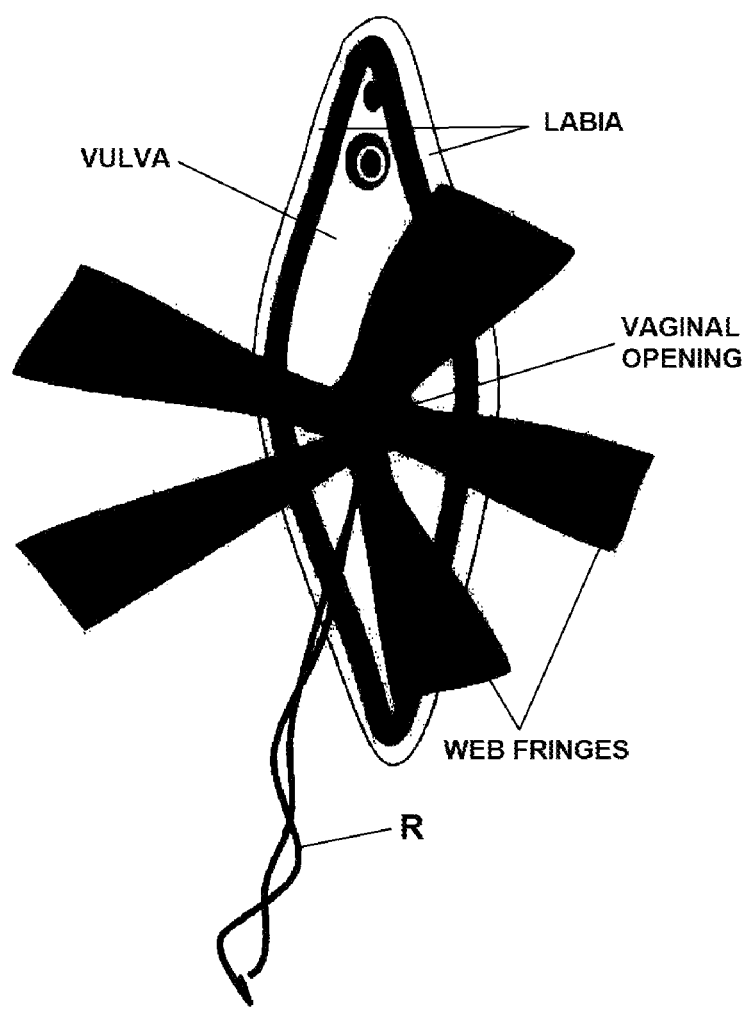
FIG. 10 shows a front view of the vulva after the insertion of a web according to an embodiment of the invention. Part of the web that is fringed protrudes outside from the vaginal cavity and the fringes form a substantially radial arrangement.
Figure 11:
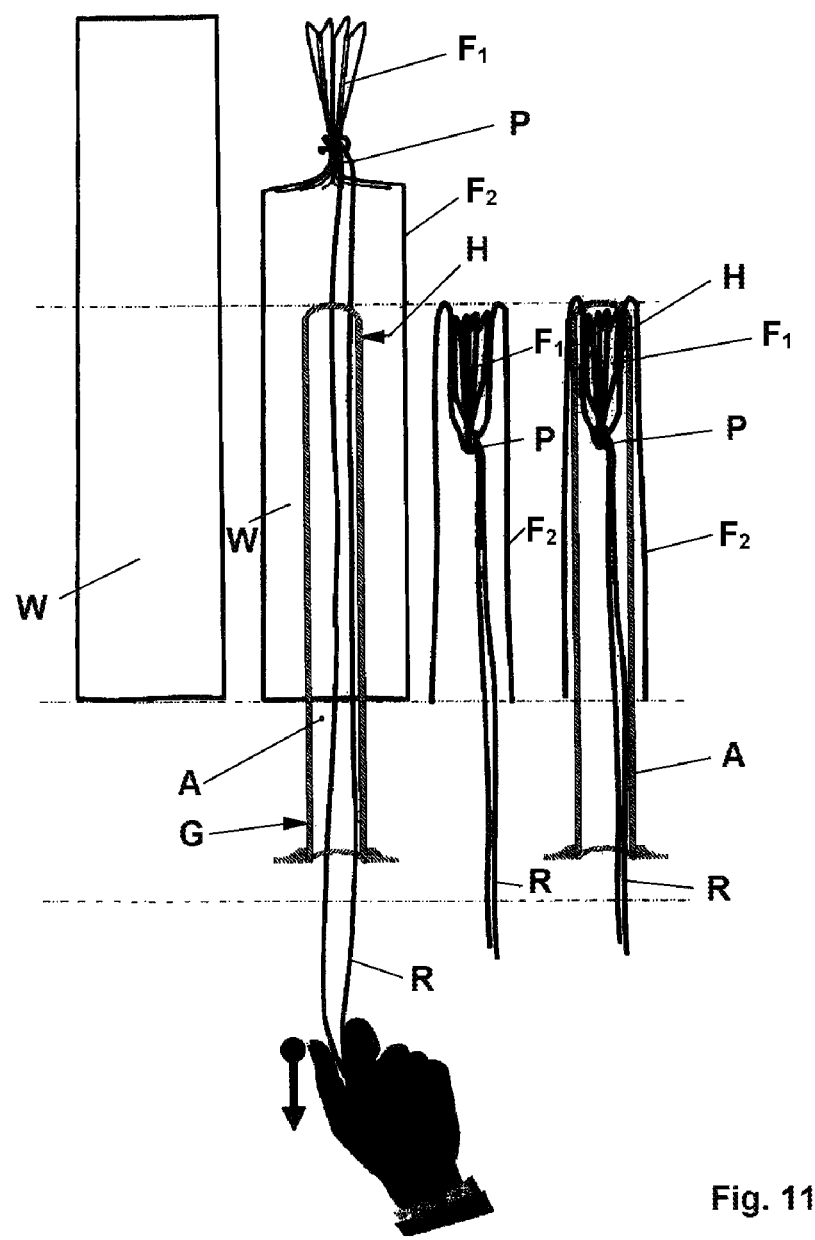

FIG. 11 illustrates the successive steps of manufacturing an assembly according to an embodiment of the invention. A flexible retention web with the desired form and dimensions, preferably a rectangular shape, is strangled along one of its transverse axis such as to form a smaller web flap where removal means are attached, for example, by knotting. The free ends of the removal means are inserted into the body of the applicator and are pulled to allow the insertion of the shorter flap F1, which is folded onto the longer flap F2 on the site P, into the hollow head portion H of the applicator A. The removal means are pulled as much as desired, to allow either partially or completely insertion of the shorter flap F2 inside the head portion H.

The invention claimed is:

1. A vaginal insertion assembly comprising:
   an at least partially hollow body applicator (A), having a grip portion (G) and a head portion (H) intended to be inserted into the vaginal cavity (V), said head portion (H) being hollow and ending with an open section (O)
   a flexible retention web (W) for insertion into the vaginal cavity of a user with the aid of said applicator (A), which web is made of an atraumatic material and is provided with means for removal (R), characterized in that
   the flexible retention web (W) is strangled at a site (P) along a transverse axis of the flexible retention web (W), thus defining a shorter web flap (F1) and a longer web flap (F2), the flexible retention web being strangled by at least one of welding, sewing, weaving, knotting, and/or adhesion,
   wherein the shorter web flap (F1) is at least partially housed within the head portion (H) of the applicator (A), with the site (P) oriented downwards, towards the grip portion (G), and with a free end (El) of the shorter web flap (F1) oriented upwards, and the longer web flap (F2) protrudes through the open section (0) and covers at least partially the body of the applicator, such that a central zone of the web remains outside the applicator.

2. The assembly according to claim 1 in which the ratio between the length (L1) of the shorter web flap, defined as the length between the site (P) and an extremity of the shorter flap (F1) opposite to the site of attachment, and the length (L2) of the longer web flap, defined as the length between the site (P) and an extremity of the longer flap (F2) opposite to the site of attachment, is at most 1/4 4.

3. The assembly according to claim 1, wherein a material of the web is chosen from nonwoven textile, polyvinyl acetate, cotton, an organic material, a plant material or a biodegradable material.

4. The assembly according to claim 1, wherein the web has reduced thickness and/or low absorbance, such that the web retains small quantities of bodily discharges and provides comfort to a user.

5. The assembly according to claim 1, wherein the shape of the web is substantially rectangular, square, oval or circular.

6. The assembly according claim 1, wherein the removal means is attached to the web at the site P and the applicator is hollow.

7. The assembly according to any claim 1, wherein the assembly is designed such that the assembly can convey at least one therapeutic or non-therapeutic agent having healing, lubricating, anticoagulant or antioxidant properties.

8. The assembly according to claim 1, further comprising a mushroom type capsule with a stalk being placed inside the head portion H on the free end El, and a cap covering the open section O.

9. The assembly according to claim 1, wherein the applicator has tubular shape.

10. The assembly according to claim 1, wherein the head of the applicator is substantially conical, having a reduced passage section relative to the diameter of the body and has radial elasticity.

11. Method of manufacturing an assembly according to claim 1, comprising the steps of:
    cutting a flexible retention web into the desired form and dimensions,
    strangling the web along its transverse axis such as to form a smaller web flap by welding, ultrasound welding, sewing, weaving, lasso-type knotting, choker-type knotting, adhesion or any method that allows a strangling effect,
    attaching to the web at least one string forming removal means in a desired point such as to allow the easy extraction of the web from the vaginal cavity,
    inserting the free ends of each string into the body of the applicator, and
    pulling the free ends of at least one string to insert at least partially the shorter flap Fl which is folded over the rest of the web material on the point of attachment P.

12. Method of manufacturing an assembly according to claim 1, comprising the steps of:
    cutting a flexible retention web into the desired form and dimensions,
    strangling the web along its transverse axis such as to form a smaller web flap by welding, ultrasound welding, sewing, weaving, lasso-type knotting, choker-type knotting, adhesion or any method that allows a strangling effect,
    attaching to the web at least one string forming removal means in a desired point such as to allow the easy extraction of the web from the vaginal cavity, and
    bending the smaller flap Fl over the rest of the web and inserting it into the applicator by pushing with the aid of an insertion member.

* * * * *